United States Patent
Stuiver et al.

(10) Patent No.: US 7,029,908 B1
(45) Date of Patent: Apr. 18, 2006

(54) PLASMIDS FOR PLANT TRANSFORMATION AND METHOD FOR USING THE SAME

(75) Inventors: Maarten Hendrik Stuiver, Oegstgeest (NL); Anne Silene Ponstein, Leiden (NL); Stephan Andreas Ohl, Leiden (NL); Oscar Johanna Maria Goddijn, Leiden (NL); Lambertus Henricus Simons, Amsterdam (NL); Bernardus Martinus Maria Dekker, Gouda (NL); Sietske Hoekstra, Oegstgeest (NL); Hendrik Tigelaar, Leiden (NL); Nicolas Elzinga, Amsterdam (NL)

(73) Assignee: Syngenta Mogen BV, Lieden (NL)

( * ) Notice: Subject to any disclaimer, the term of this patent is extended or adjusted under 35 U.S.C. 154(b) by 0 days.

(21) Appl. No.: 09/469,812

(22) Filed: Dec. 22, 1999

Related U.S. Application Data

(63) Continuation of application No. PCT/EP98/04171, filed on Jun. 29, 1998.

(30) Foreign Application Priority Data

Jun. 30, 1997 (EP) .................................. 97201990

(51) Int. Cl.
*C12N 15/82* (2006.01)
(52) U.S. Cl. ................................. 435/320.1
(58) Field of Classification Search ............. 435/320.1, 435/468, 469, 419, 252.3; 800/278, 285, 800/286, 288, 294
See application file for complete search history.

(56) References Cited

U.S. PATENT DOCUMENTS 4,710,464 A  12/1987  Belagaje et al. ......... 435/91.41
5,658,772 A *  8/1997  Odell et al. ............... 435/172.3
6,521,458 B1 *  2/2003  Gutterson et al. .......... 435/469

FOREIGN PATENT DOCUMENTS

EP   0 687 730 A1   12/1995
WO   WO 96/21725    7/1996
WO   WO 96/26283    8/1996

OTHER PUBLICATIONS

Ramanathan, V. and Veluthambi, K.,"Transfer of non-T-DNA portions of the *Agrobacterium tumefaciens* Ti plasmid pTiA6 from the left terminus of TL-DNA." 1995, Plant Molecular Biology, vol. 28, pp. 1149-1154*
D'Souza-Ault et al 1993, J. Bacteriology 175(11):3486-3490.*
Gleave, A., Plant Molecular Biology, vol. 20, pps. 1203-1207, 1992.
Tinland, B., et al., EMBO Journal, vol. 14, No. 14, pps. 3585-3595, 1995.
van der Graaff, E., et al., Plant Molecular Biology, vol. 31, pps. 677-681, 1996.
D'Souza-Ault, M., et al., Journal of Bacteriology, vol. 175, No. 11, pps. 3486-3490, Jun. 1993.
Kononov, M., et al., The Plant Journal, vol. 11, No. 5, pps. 945-957, 1997.

* cited by examiner

*Primary Examiner*—David H Kruse
(74) *Attorney, Agent, or Firm*—Syngenta Mogen BV

(57) ABSTRACT

The invention provides novel Ti-plasmid vectors for *Agrobacterium*-medicated plant cell transformation. Plamsids of the invention are constructed with a DNA sequence (ie., a negative selectable maker or a DNA sequence that inhibits DNA unwinding) flanking the T-DNA bordered gene of interest that reduces or eliminates the occurrence of transformants with vector read-through DNA sequence. The invention also provides methods of plant cell transformation utilizing these novel vectors.

8 Claims, 2 Drawing Sheets

PLASMIDS FOR PLANT TRANSFORMATION AND METHOD FOR USING THE SAME

This application is a continuation of pending international application number PCT/EP98/04171, filed Jun. 29, 1998.

FIELD OF THE INVENTION

This invention relates to the *Agrobacterium* mediated plant transformation, especially to transformation of plants with T-DNA, where accidental transfer of non-T-DNA vector sequences is prohibited.

DESCRIPTION OF THE RELATED ART

Transformation of plants by using *Agrobacterium* and the Ti or RI plasmids present in wild-type *Agrobacterium* bacteria has been known since 1983 (e.g. in EP 0 116 718 and EP 0 120 516). This transformation procedure generally consists of infection of plants with non-tumorigenic *Agrobacterium* strains which have been provided with a heterologous gene. This heterologous gene is located on a plasmid in a piece of so-called T-DNA, which is the DNA located between two imperfect direct repeats of about 24 basepairs length, the T-DNA borders. Transfer of the heterologous gene into the plant takes place in a process wherein the also on the plasmid located vir-genes are activated through phenolic compounds by incubation of Agro-bacterium with plant cells. These vir-proteins (D1 and D2) cause nicking of the border repeats at a precise site, whereby the T-DNA is cut at the T-DNA borders from the plasmid and inserted into the plant genome.

The right border region seems to be the most essential in T-DNA transfer: Ti-plasmids with the T-DNA right border region deleted are avirulent (Holsters, M. et al., Plasmid 3, 212–230, 1980). Deletion of the left border region has no effect on virulence (Joos, H. et al., Cell 32, 1057–1067, 1983).

The necessity for the T-DNA borders to be present remains when the transformation is done using a binary vector system, in which the T-DNA is located on a separate independent replicon, the binary vector.

After transformation the T-DNA is present in the genomes of the host plants as single units or in multiple, tandemly arrayed copies. However, truncated T-DA regions are also frequently observed (Deroles S. C. and Gardner, R. C., Plant Mol. Biol. 11, 365–377, 1988). More recently, there is information that also DNA beyond the borders is integrated into the genome of the host plants. Such is reported to be the case in 20 to 30% of the transgenic plants (Martineau, B. et al., The Plant Cell 6, 1032–1033, 1994). However, very recently, a report in the literature conveyed that approximately 75% of tobacco transformants contained vector 'backbone' sequences (Kononov, M. E. et al.. The Plant J. 11 (5), 945–957, 1997).

Another phenomenon that is sometimes occurring is that the to transfer of T-DNA starts on the left border, which can also act as a (weak) starting point. Then the amount of DNA which is 'read-through' can be substantial: it is found that sometimes the transfer, which starts at the left border, reads through the right border and ends again at the left border, resulting in transfer of the complete binary vector (van der Graaff, E. et al., Plant Mol. Biol. 31, 677–681, 1996).

Since it will be the aim of the plant geneticist to transfer only the DNA that is present in the T-DNA a prohibition of both read-through mechanisms would be welcomed. Furthermore, registration authorities, dealing with requests for (market) registration of transgenic plants and/or transgenic food, also are of the opinion that contamination of transgenic plants with vector DNA should be avoided as much as possible.

BRIEF SUMMARY OF THE INVENTION

The invention comprises a vector for plant transformation comprising a T-DNA with flanking T-DNA borders, characterized in that the vector further comprises a nucleic acid sequence which prevents the development of plant transformants having more vector sequences than the T-DNA sequence.

This sequence which prevents the development of transformants having more vector sequences than the T-DNA sequence is a gene coding for a toxic compound, preferably selected from the group of RNAse, DNAse, phytotoxins, diphteria toxin, proteases and antisense housekeeping genes, such as ATP synthase, cytochrome c, pyruvate kinase, aminoacyl transferase, or phosphate, di-, tricarboxylkate and 2-oxo-glutarate translocators.

Another embodiment of said vector is when the sequence which prevents the development of transformants with vector sequences outside the T-DNA sequence comprises a sequence which binds DNA-binding proteins, or which is high in its G+C-content.

Also part of the invention is a method for obtaining transgenic plants which do not contain vector sequences outside the T-DNA by transforming plants with a vector according to the invention. Next, hosts containing such a vector, like bacteria, preferably a member of the Agrobacteriaceae, more preferably *Agrobacterium* or Rhizobacterium, most preferably *Agrobacterium tumefaciens* form also part of the invention.

Furthermore, a method for the transformation of plants characterized in that a vector according to the invention is used is comprised in the invention.

DETAILED DESCRIPTION OF THE INVENTION

Figure 1:
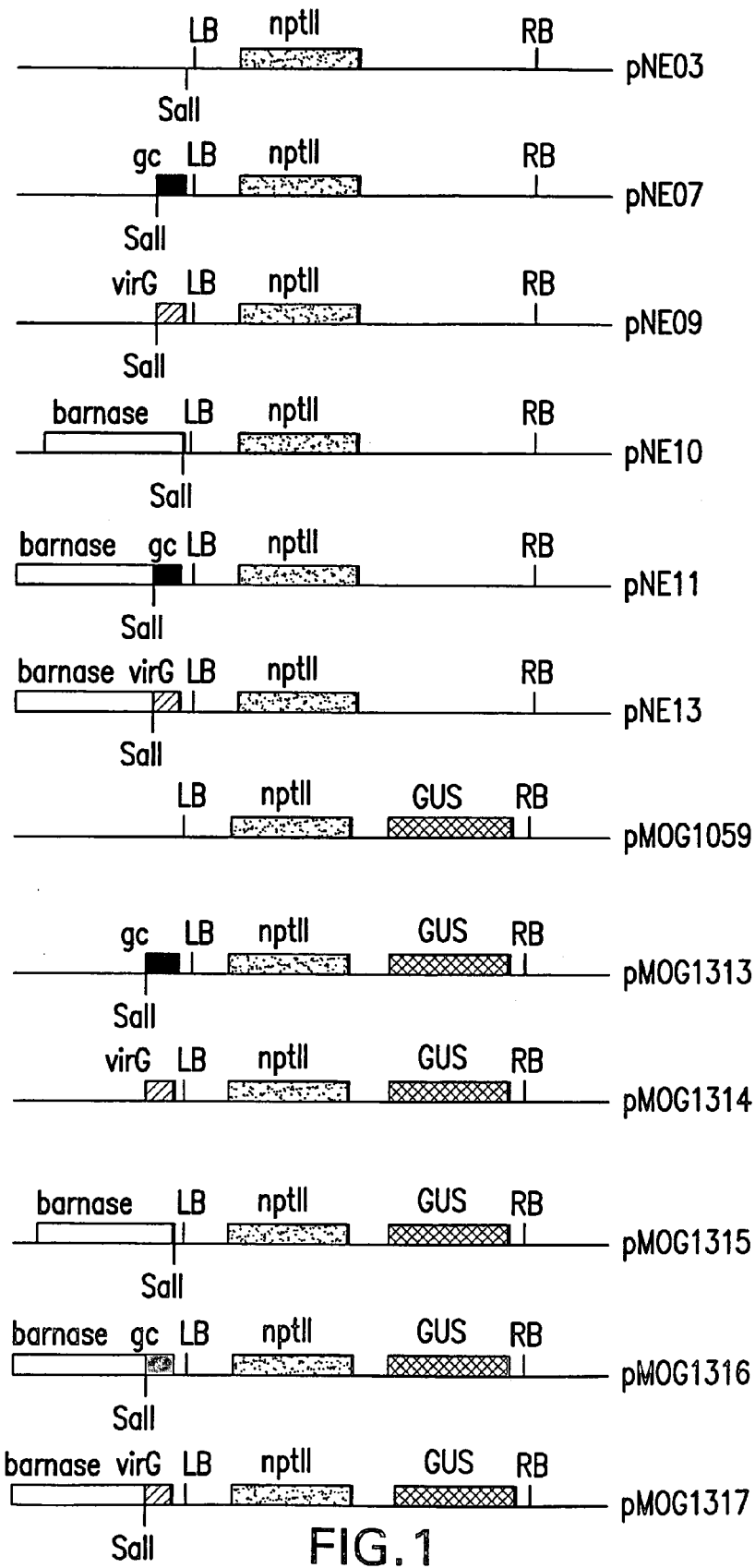
FIG. 1. Schematic representation of constructs used.

Basically all known plasmids and vectors which are used for plant transformation can be adapted to a vector according to the invention or a vector usable in a method according to the invention. Examples of such plasmids are pBin19 (Bevan, M., Nucl. Acids Res. 12, 8711–8721, 1984), pMOG101 (WO 93/10251), pMOG800 (WO 95/05467), pMON128 (EP 0 131 623), GV2260 (Deblaere et al. 1985, Nucl. Acids Res. 13, 4777–4788), etcetera and all plasmids derived from them.

The key characteristics of such plasmids are that they contain T-DNA flanked by T-DNA border sequences. Furthermore, they must be suited to replicate in *Agrobacterium*, thus they should contain an origin of replication (ori) sequence suitable for use in *Agrobacterium*. Although the *Agrobacterium*-strains which are most frequently used are *A. tumefaciens*, also *A. rhizogenes* is suitable for transformation of plants. Here, the transformatable DNA is located on the Ri-plasmid and this DNA should thus subsequently have to be called R-DNA. However, T-DNA is the term commonly used, and this does not limit the invention to only *A. tumefaciens*, but includes all transformation methods in which a DNA sequence located between two direct repeats is used in transformation to plants.

For transformation, next to the T-DNA also virulence proteins are necessary. These can be coded for on the same plasmid which also contains the T-DNA, which in this constellation generally is referred to as a co-integrate plasmid. It can equally well be the case that the virulence genes are located on a separate plasmid (the the system is usually referred to as the binary vector system) or even on the bacterial chromosome.

Furthermore, the plasmids will normally also contain a gene coding for a resistance to an antibiotic (enabling culturing under selection pressure), and an ori for replication in *E. coli*.

A general introduction on the transformation of genes into plants and the role of *Agrobacterium* and the Ti-plasmid therein can be found in the handbook of "Principles of gene Manipulation" (Old, R. W. and Primrose, S. B., Blackwell Scientific Publications, London, 1994, Chapter 14, pp. 268–301).

One embodiment of the invention comprises a vector in which a gene coding for a toxin under the control of a plant-expressible promoter is located outside the T-DNA borders. It is essential that this gene is not toxic for or not expressed in the bacterium because that would deteriorate the bacterium and with it the capability of transformation of the T-DNA to the plant. There are several ways in which toxic effects for the bacterium can be prevented. One of them is to choose a toxic compound that is not toxic to the bacterium. An example of such a toxic compound is diphteria-toxin. Similarly, also the antisense approach in which an essential plant house-keeping gene is knocked out gives opportunities to prevent bacterial deterioration. For this it must be kept in mind to choose a house-keeping gene which is active (and essential) in plants, but which lacks or has only a minor function in bacteria or is not homologous enough to be hampered by antisense expression of the gene.

However, even if the toxins are harmful to bacteria, ways can be found to prevent expression of said toxins in the bacteria. One possibility to accomplish this is by producing a gene construct in which the toxin is under control of a plant promoter. Although not all plant-specific promoters can be used in such a vector, since they give at least some expression in bacteria, it is easy to establish if a promoter of choice does not yield expression in bacterial cells (for instance by transforming a bacterium with a GUS-gene preceded by said promoter; expression of GUS in the bacteria can easily be assayed). Finally, a way to prevent expression in bacteria is to introduce an intron sequence into the coding sequence of the toxin (or to use intron-containing genomic sequences). Since bacteria are unable to excise introns only a non-functional (part of the) protein will be produced, which do not harm the bacteria.

Toxins which can be used comprise toxins specific for certain plants, but also the more general available toxins which act on membrane systems and/or other general cell structures or processes can be used. Examples of such toxins are: RIP, magainins, RNAses (like barnase), DNAses, proteases, etcetera.

Other approaches can be applied in several ways, and genes for these approaches may be selected from the group consisting of (a) genes encoding ribozymes against an endogenous RNA transcript, (b) genes which produce proteins which are able to evoke a hypersensitive reaction, (c) genes which when transcribed produce RNA transcripts that are complementary or at least partially complementary to RNA transcripts of endogenous genes that are essential for cell viability, a method known as antisense inhibition of gene expression (disclosed in EP-A 240 208), and (d) genes that when transcribed produce RNA transcripts that are identical or at least very similar to transcripts of endogenous genes that are essential for cell viability, an as yet not fully understood way of inhibition of gene expression referred to as co-suppression (disclosed by Napoli C. et al., 1990, The Plant Cell 2, 279–289).

Evoking a hypersensitive response (HR) is possible when a pathogen-derived elicitor protein and a corresponding plant-derived receptor protein are expressed simultaneously. Couples of such corresponding elicitor/receptor genes and their applicability to evoke a HR in a transgenic plant, are known in the art, e.g. for *Cladosporium fulvum* avr-genes and *Lycopersicon esculentum* Cf-genes (WO 91/15585) or for Psuedomonas syringae avr-genes and *Arabidopsis thaliana* RPM1-genes (Grant M. R., et al., Science 269, 843–846, 1995). The general idea of the application of these genes in this invention is co insert one of the genes between the I-DNA borders and the complementary gene outside the borders. Thus, when DNA from outside the borders is transferred to the plant both genes will be expressed and a hypersensitive response will be produced, which will kill the thus transformed cell.

Since the plant-derived resistance genes occur naturally in some of the plants it is possible for those plants to suffice with a gene coding for the corresponding avirulence gene situated outside the T-DNA borders. When expressed after transformation it will encounter the endogenously produced corresponding plant gene and evoke a HR response.

Preferred embodiments of the constructs for this HR-mechanism (in view of regulatory restrictions) are constructs in which the plant-derived gene is present between the T-DNA borders and the pathogen-derived gene is present outside the borders.

According to another embodiment of the invention use is made of antisense genes to inhibit expression of endogenous genes essential for cell viability, which genes are expressed in the plant cell.

Target genes for antisense disrupter genes are selected from those coding for enzymes that are essential for cell viability, also called housekeeping enzymes, and should be nuclear encoded, preferably as single copy genes, although those encoded by a small size gene family would also be suitable for the purpose of the invention. Furthermore, the effect of antisense expression of said genes must not be nullified by diffusion or translocation from other cells or organelles of enzyme products normally synthesized by such enzymes. Preferably, genes coding for membrane-translocating enzymes are chosen as these are involved in establishing chemical gradients across organellar membranes. Inhibition of such proteins by antisense expression can not, by definition, be cancelled by diffusion of substrates across the membrane in which these proteins reside. The translocated compound is not limited to organic molecules but can be of inorganic nature; e.g. P, H, OH or electrons.

A list of target enzymes is given in Table 1 by way of example but the invention is not limited to the enzymes mentioned in this table. More detailed listings can be assembled from series as Biochemistry of Plants (Eds.

Stumpf & Conn, 1988–1991, Vols. 1–16 Academic Press) or Encyclopedia of Plant Physiology (New Series, 1976, Springer-Verlag, Berlin).

Although only in some cases, the genes coding for these enzymes have been isolated and, therefore, the number of gene copies are not known, the criteria that have to be met are described in this invention.

EXAMPLES OF TARGET ENZYMES FOR ANTISENSE AND SENSE EXPRESSION

| enzyme | pathway/organelle |
| --- | --- |
| ATP synthase | mitochondrion |
| adenine nucleotide translocator | mitochondrion |
| phosphate translocator | mitochondrion |
| tricarboxylate translocator | mitochondrion |
| dicarboxylate translocator | mitochondrion |
| 2-oxo-glutarate translocator | mitochondrion |
| cytochrome C | mitochondrion |
| pyruvate kinase | glycolysis |
| glyceraldehyde-3P-dehydrogenase | glycolysis |
| NADPH-cytochrome P450 reductase | lipid metabolism |
| fatty acid synthase complex | lipid metabolism |
| glycerol-3P-acyltransferase | lipid metabolism |
| hydroxymethyl-glutaryl CoA reductase | mevalonic acid pathway |
| aminoacyl transferase | nucleic acid metabolism |
| transcription factors | nucleic acid metabolism |
| elongation factors | nucleic acid metabolism |

To maximize the antisense effects in a plant host, the use of homologous genes is preferred. With homologous is meant obtainable from the same plant species as the plant host. Heterologous, for the purpose of this specication shall mean obtainable from a different plant or non-plant species. Heterologous shall also comprise synthetic analogs of genes, modified in their mRNA encoding nucleic acid sequence to diverge at least 5% of the host gene. As housekeeping genes are in general highly conserved, heterologous probes from other (plant) species can be used to isolate the corresponding gene from the crop species that is to be made resistant. Such gene isolations are well within reach of those skilled in the art and, in view of the present teaching require no undue experimentation.

As regards the necessity of a transcriptional terminator region, it is generally believed that such a region enhances the reliability as well as the efficiency of transcription in plant cells. Use thereof is therefore strongly preferred in the context of the present invention.

Another embodiment of the present invention is a vector in which read-through or starts of DNA-transfer from the left border are inhibited by insertion of a nucleotide sequence outside the T-DNA borders that interferes with the DNA unwinding process naturally needed for formation of a DNA molecule intended for translocation to the plant.

An example of such a sequence is a GC-rich sequence of approximately 40 nucleotides (preferable 20–60 basepairs), of which DNA unwinding is energetically unfavourable, and thus is expected to hamper unwinding of DNA through this sequence. However, also other sequences may be used which are blocking read-through or left-border starts. Calculations as to the increased stability of such doublestranded sequences are known to the person skilled in the art, and are described in Maniatis, Fritsch and Sambrook: Molecular Cloning, a laboratory manual, Cold Spring Harbor, 1982, pp 388.

Another example of a nucleotide sequence which will hamper the DNA unwinding process in sequences outside the T-DNA border is a sequence consisting of binding sites for *Agrobacterium* DNA-binding proteins. Displacement of bound double-stranded DNA-binding proteins will be required for unwinding of the DNA, so that the energy required for strand displacement is increased considerably. In addition, the presence of DNA-bound proteins close to the left border may physically interfere with assembly of the DNA-protein complex needed for unwinding of the DNA downstream of the left border.

In general, all double-stranded-DNA-binding proteins will be able to interfere with this process. Preferably, protein binding sites are used of which the DNA-protein interaction can be induced or strengthened by treatment of *Agrobacterium* cells with an external stimulus. More preferably, the DNA-binding protein is virG, which is also an activator protein for all vir proteins involved in T-DNA mobilization and transfer. VirG is known to bind to the vir box, consisting of the sequence 5'TNCAATTGAAAY3' (SEQ ID NO: 19) (in which N is any nucleotide and Y is a pyrimidine base nucleotide (T or C)). Binding of virG to this vir box is thought to be initiated or augmented upon activation of the *Agrobacterium* through the virA/virG two-component regulatory system. In vivo, activation of vir genes is dependent on phosphorylation of virG, but the actual role of this modification is not yet known. As outlined in Sheng and Citovsky (The Plant Cell 8, 1699–1710, 1996) a very likely explanation is that phosphorylated virG protein has an increased affinity for its cognate binding site.

Also, introduction of binding sites for bound DNA-binding proteins closely linked to the left border sequences can physically interfere by steric hindrance with the assembly of proteins on this left border needed for strand displacement, thus effectively reducing starts at the left border.

Although some of the embodiments of the invention may not be practicable at present, e.g. because some plant species are as yet recalcitrant to genetic transformation, the practicing of the invention in such plant species is merely a matter of time and not a matter of principle, because the amenability to genetic transformation as such is of no relevance to the underlying embodiment of the invention.

Transformation of plant species is now routine for an impressive number of plant species, including both the Dicotyledoneae as well as the Monocotyledoneae. In principle any transformation method may be used to introduce chimeric DNA according to the invention into a suitable ancestor cell. A preferred method according to the invention comprises *Agrobacterium*-mediated DNA transfer. Especially preferred is the use of the so-called binary vector technology (as disclosed in EP A 120 516 and U.S. Pat. No. 4,940,838).

Tomato transformation is preferably done essentially as described by van Roekel et al. (Van Roekel, J. S. C., Damm, B., Melchers, L. S., Hoekema, A. (1993)). Factors influencing transformation frequency of tomato (*Lycopersicon esculentum*). (Plant Cell Reports, 12, 644–647). Potato transformation is preferably done essentially as described by Hoekema et al. (Hoekema, A., Huisman, M. J., Molendijk, L., van den Elzen, P. J. M., and Cornelissen, B. J. C. (1989)). The genetic engineering of two commercial potato cultivars for resistance to potato virus (X. Bio/Technology 7, 273–278).

Although considered somewhat more recalcitrant towards genetic transformation, monocotyledonous plants are amenable to transformation and fertile transgenic plants can be regenerated from transformed cells or embryos, or other plant material. Monocotyledonous plants, including commercially important crops such as rice and corn are amenable to DNA transfer by *Agrobacterium* strains (vide WO 94/00977; EP 0 159 418 B1; Gould J, Michael D, Hasegawa O, Ulian EC, Peterson G, Smith RH, (1991) Plant. Physiol. 9, 426–434).

It is known that practically all plants can be regenerated from cultured cells or tissues. The means for regeneration vary from species to species of plants, but generally a suspension of transformed protoplasts or a petri plate containing transformed explants is first provided. Shoots may be induced directly, or indirectly from callus via organogenesis or embryogenesis and subsequently rooted. Next to the selectable marker, the culture media will generally contain various amino acids and hormones, such as auxin and cytokinins. It is also advantageous to add glutamic acid and proline to the medium, especially for such species as corn and alfalfa. Efficient regeneration will depend on the medium, on the genotype and on the history of the culture. If these three variables are controlled regeneration is usually reproducable and repeatable. After stable incorporation of the transformed gene sequences into the transgenic plants, the traits conferred by them can be transferred to other plants by sexual crossing. Any of a number of standard breeding techniques can be used, depending upon the species to be crossed.

Experimental Part

EXAMPLE 1

Construction of a Binary Vector Backbone

A unique Sal I restriction endonuclease site was introduced into pMOG 800 so that elements aimed at inhibition of readthrough or counterselection of transgenics carrying vector sequences, can be cloned next to the left border. The site is located 10 bp adjacent to the left border. Using a simple PCR based mutagenesis strategy with primers SEQ ID NO: 1 to SEQ ID NO: 4 a fragment encompassing the DraIII and NruI unique sites was created that is near-identical to the corresponding fragment in the binary vector pMOG800 (deposited at the Centraal Bureau voor Schimmelcultures, Baarn, The Netherlands, under CBS 414.93, on Aug. 12, 1993), with an additional unique SalI site 10 bp from the left border repeat, outside the T-DNA.

This PCR fragment was digested with DraIII and NruI and cloned into pMOG800 digested with DraIII and NruI. The resulting plasmid is called pNE03.

EXAMPLE 2

Insertion of the GC-Rich Stretch

A 40 bp GC-rich stretch was created by annealing SEQ ID NO:5 and -6 to each other. Insertion of this fragment into a SalI site will leave a SalI site at only one end intact. The double stranded synthetic oligo was phosphorylated by T4 polynucleotide kinase and cloned into the SalI-digested pNE03 vector. The resulting plasmid pNE07 has the GC-rich stretch inserted at the SalI site, which results in removal of the SalI site at the side nearest the left T-DNA border. A schematic representation of the orientation is presented in FIG. 1.

EXAMPLE 3

Insertion of virG Binding Sites

The fragment containing VirG binding sites is derived from the VirB promoter of *Agrobacterium* strain ERA 101. The VirB promoter was previously shown to contain two vir-box sequences which are both recognized by VirG (Das and Pazour, 1989, Nucl. Acids Res. 17, 4541–4150). The Vir-box alone is thought not to be sufficient for binding of the VirG protein, additional specific nonconserved sequences 3' to the Vir-box, approximately 19 bp, are most likely also required for binding of the VirG protein. The primers SEQ ID NO: 7 and -8 were used for PCR amplification of an appr. 90 bp VirB promoter fragment from *Agrobacterium tumefaciens* strain MOG101. The fragment was digested with SalI and AvaI, and introduced into the unique Sal I site of the pNE03 vector. Again this fragment is oriented so that the SalI-AvaI ends are joined closest to the Left Border. A schematic representation of the orientation is presented in FIG. 1. This vector is denominated pNE09.

EXAMPLE 4

Introduction of a Barnase Expression Cassette

The barnase open reading frame and nos terminator sequences (925 bp) were excised from pMOG 944 (WO 98/22599) using the NcoI and EcoRI sites and cloned into pMOG1302 digested with NcoI and EcoRI. pMOG1302 contains a GapC promoter fragment (Shih et al. 1991, Gene 104, 133–138) and has a pMOG445 (pUC-based) vector backbone (pMOG445 was made from pUC18 (Yannisch-Perron and Messing, 1985, Gene 33, 103–119) by insertion of a double-stranded synthetic DNA made with primers SEQ ID NO: 9 and SEQ ID NO: 10 into pUC18 digested with EcoRI and SstI). The resulting plasmid has the barnase Open Reading Frame and nos 3' untranslated sequences/terminator coupled to the GapC promoter and 5' untranslated sequences on the NcoI site, situated on the start codon. The resulting plasmid is called pNE01. The whole expression cassette of pNE01 (GapC-barnase-nos) was subseqeuntly cloned into PBSK+ (Stratagene, La Jolla, Calif., USA) using the BamHI and XhoI sites. This plasmid is called pNE05. Then pNE05 was digested with BamHI and an adaptor (SEQ. ID. NO: 11) which destroys the BamHI site and introduces a SalI site was introduced. The resulting plasmid is pNE08. The expression cassette was then lifted out of pNE08 using SalI and XhoI and cloned into the modified binary vectors pNE03, pNE07 and pNE09 all digested with SalI. This results in vectors pNE10 (barnase cassette only), pNE11 (GC clamp+barnase cassette) and pNE12 (virG binding sites+barnase cassette).

EXAMPLE 5

Introduction of a GUS Marker Cassette

An EcoRI-HindIII fragment from pMOG1059 contained a GUS expression cassette containing 1) the FdrolD chimeric promoter and untranslated sequences (Patent Appl. No. 97203912.7 filed Dec. 12, 1997), 2) a GUS Open Reading Frame containing an StLS1 intron (Vancanneyt et al., 1990, Mol. Gen. Genet. 220–245–250) and 3) 3' untranslated/terminator sequences of the proteinase inhibitor II gene (Thornburg et al., 1987, Proc. Natl. Acad. Sci. USA 84, 744–748). This EcoRI-HindIII fragment was inserted into the EcoRI-HindIII sites of binary vectors pNE10, -11 and -12 between the borders. The GUS cassette is closest to the Right Border, the nptII selection marker cassette is found closest to the Left Border (see FIG. 1). As an unmodified control pMOG1059 was used, of which the vector sequences are the unmodified pMOG800 backbone. pMOG1313 is the binary vector that has the FdrolD-GUS cassette on the T-DNA and contains the GC clamp next to its left border, pMOG1314 identical within the T-DNA, but contains the virG binding sites next to the left border, pMOG1315 again has the same T-DNA sequences and contains the barnase cassette next to the left border. Likewise, pMOG1316 contains both the GC clamp and the barnase cassette and pMOG1317 the virG binding sites followed by the barnase cassette.

EXAMPLE 6

Analysis of Potato Transformation Frequency With the Novel Binary Vectors

Potato stem segments of cv. Kardal were transformed with *Agrobacterium tumefaciens* strain ERA 105 in three separate transformation experiments using a standard transformation protocol (as described in PCT/EP 98/02979). Per construct a minimum of 150 explants were used. Usually this will lead to regeneration of about 90 transformants/construct. Transformation frequency was determined as the number of regenerants able to root under selective pressure on kanamycin-containing growth medium relative to the number of explants used. For Table 2 we normalized the transformation frequency to 1.0 for the control construct pMOG1059.

Table 2. Average relative transformation frequencies observed with constructs tested. All values were normalized per transformation experiment to pMOG1059 (set at 1.00). The values were averaged from three independent transformation experiments.

| Construct | description | Transformation Frequency |
|---|---|---|
| pMOG1313 | GC clamp | 1.35 |
| pMOG1314 | virG binding sites | 1.24 |
| pMOG1315 | barnase cassette | 0.97 |
| pMOG1316 | GC + barnase cassette | 0.85 |
| pMOG1317 | virG + barnase cassette | 0.90 |

Insertion of a GC-clamp or viRG binding sites outside the left border appears to increase the transformation frequency somewhat. We do not completely understand the reason for this effect. One explanation is that the interference with left border starts of DNA transfer (as was noted to happen by some investigators (Kononov. M. E. et al., 1997. Plant J. 11, 945–957; Ramanathan, V. and Veluthambi, K., 1995, Plant Mol. Biol. 28, 1149–1154) will increase the chances of T-DNA transfer, which will increase the number of initial transformed cells with the nptII selction marker.

EXAMPLE 7

Analysis of Vector Backbone Co-Integration

Next we analyzed the presence of DNA fragments spanning the left and right T-DNA borders by PCR, fragments indicative of integration of vector DNA in transformants. Per construct, 75 individual lines were analyzed for outer border sequences by a multiplex PCR. Six primers were used for the multiplex PCR with npt II primers as an internal control. For the location of primers on the binary vectors see FIG. 2.

Left border spanning sequences from transformants made with the vectors pMOG 1313, pMOG 1314 and pMOG 1059 were amplified using primers SEQ ID NO: 12 and SEQ ID NO: 13, which yields a fragment of approx. 1200 bp. For transformants made with constructs pMOG 1315, pMOG 1316 and pMOG 1317 primers SEQ ID NO: 12 and SEQ ID NO: 14 were used for amplification of left border spanning sequences. The outside primer in this case anneals to the barnase gene. This primer was chosen because otherwise the PCR fragment would be too large to permit efficient amplification. PCR amplification with primers for the internal control, npt II, SEQ ID NO: 15 and SEQ ID NO: 16, will give a fragment of approx. 850 bp. For sequences encompassing the right border a 500 bp fragment was amplified using primer SEQ ID NO: 17 and SEQ ID NO: 18. The PCR reactions were carried out on a Perkin-Elmer 480 thermal cycler.

After amplification the obtained PCR fragments were electrophoresed on a 0.8% agarose gel containing Ethidium Bromide. After photography the different fragments were counted and the percentage of readthrough determined (see Table 3 for compilation).

Table 3: Percentages of individual transformants with sequences spanning the left and right borders.

| construct | LB only | RB only | LB + RB both present | Sum of lines with border transitions |
|---|---|---|---|---|
| pMOG 1313 | 2.82% | 16.90% | 28.17% | 47.89% |
| pMOG 1314 | 4.76% | 12.70% | 20.63% | 38.10% |
| pMOG 1315 | 4.17% | 6.94% | 2.78% | 13.89% |
| pMOG 1316 | 4.35% | 4.35% | 1.45% | 10.14% |
| pMOG 1317 | 5.56% | 5.56% | 1.39% | 12.50% |
| pMOG 1059 | 2.90% | 8.70% | 37.68% | 49.28% |

As can be seen from table 2 the number of lines that show the unwanted co-integration of vector sequences is very high. Approximately half of our transgenic lines made with the unmodified pMOG1059 construct have integration of at least part of the vector backbone. This value is not reduced when a GC-rich stretch is introduced next to the left border. The introduction of virg binding sites next to the left border appears to reduce the number of border transitions somewhat. Clearly, when the GC-rich stretch or the virG binding sites are introduced outside the left border, there is a pronounced reduction in the number of lines with left border transitions (calculated as the percentage of lines carrying either LB only or LB plus RB transitions), reducing from 40% in pMOG1059 to approximately 30% and 25% in the pMOG1313 and pMOG1314-transformed lines.

Construct pMOG1315, carrying just the barnase expression cassette outside the left border has a very significantly reduced number of transformants with vector sequences. Combining either the GC stretch or the virG binding sites with the barnase cassette appears to reduce the number further. In our experiments we see the number of individual lines with border transitions drop to about 10% which is a very significant improvement relative to the unmodified pMOG1059 control.

A brief survey of primary tomato transformants in our collection indicated that about 40% of the transgenic tomato plants contained outer border sequences. This clearly indicates the need for this technology also in other plant species.

EXAMPLE 8

Figure 2:
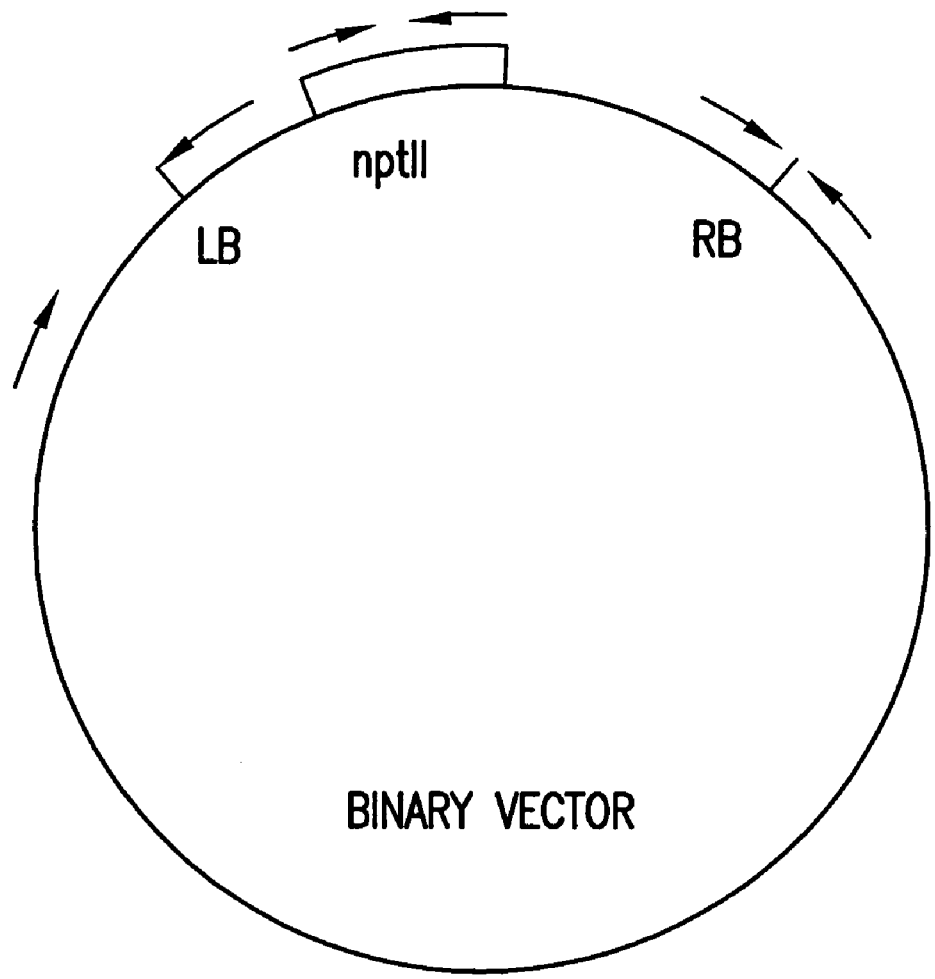
FIG. 2: Schematic representation of the location of hybridization of the primers which were used to check for co-integration of vector sequences.

Use of Avirulence and Resistance Genes for Counterselection of Vector Sequences Outside the T-DNA The *Pseudomonas Syringae*-derived AvrRpm1 elicitor coding region is cloned operatively behind a strong constitutive promoter, and before a the potato proteinase inhibitor II transcriptional terminator sequence. This cassette is introduced into the BglII site downstream of the left T-DNA border. A genomic DNA fragment containing the *Arabidopsis thaliana* derived Rpm1 resistance gene flanked by a constitutive promoter and terminator sequences is introduced into the T-DNA, thus forming pMOG 1257 (FIG. 2). Transformation of Brassic napus, tomato and potato plants with this construct is performed using standard procedures.

Transgenic plants arising from this transformation procedure are analysed for their presence of vector sequences outside the T-DNA by using a PCR reaction on genomic DNA of each of the transformants. The primers used span a sequence of appr. 300 bp outside the T-DNA close to the left border.

EXAMPLE 9

Determination of Copy Number

For determination of the copy number of the plants containing construct pMOG1317 and the control plants containing construct pMOG1059 genomic DNA was isolated from leaves of 25 plants per line using a CTAB extraction procedure essentially as described (Rogers and Bendich, 1985, Plant. Mol. Biol. 5, 69–76). About 10 µg of genomic DNA was digested with the restriction enzyme EcoRI in the appropriate buffer for 16 hours at 37° C. This restriction site is located once in both constructs, between the GUS expression cassette and the NPT-II cassette. The digestion mixtures were extracted with 1 volume phenol:chloroform:isoamylalcohol (25:24:1, v/v, Gibco BRL) and precipitated with 0.1 volume of 3 M NaAc (pH=5.2) and 2.5 volumes of 96% ethanol. The DNA pellet was washed with 70% ethanol and the pellet was then dissolved in 20 µl distilled water.

Each sample was separated on a 0.7% agarose gel for approximately 16 hours at 2V/cm. The DNA was transferred to a nylon membrane (Hybond-N+, Amersham Life science) using southern blotting with 0.4 M NaOH. The blot was hybridized (16 hours, 65° C.) using a 558 bp GUS fragment (NcoI-EcoRV fragment of pMOG18; Sijmons et al., Biotechnology vol. 8, March 1990, page 217–221) labeled with 32P-dCTP as a probe. Then the blot was washed with a stringency of 0.2×SSC at 65° C. The results of the southern blot are listed in Table 4.

Table 4. Number of T-DNA inserts observed in various individual lines transformed with pMOG1059 and pMOG1317.

| pMOG1059 line | copy number | pMOG1317 line | copy number |
|---|---|---|---|
| 66 | 5 | 1 | 3 |
| 67 | 5 | 2 | 1 |
| 68 | 1 | 3 | 1 |
| 69 | 2 | 5 | 1 |
| 70 | 3 | 6 | 4 |
| 71 | 3 | 7 | 4 |
| 72 | 3 | 8 | 2 |
| 73 | 5 | 9 | 2 |
| 74 | 6 | 11 | 1 |
| 76 | 2 | 12 | 1 |
| 77 | 9 | 14 | 1 |
| 78 | 3 | 15 | 3 |
| 79 | 4 | 16 | 2 |
| 80 | 2 | 17 | 4 |
| 81 | 3 | 18 | 3 |
| 82 | 1 | 19 | 2 |
| 83 | 3 | 20 | 1 |
| 85 | 1 | 21 | 3 |
| 86 | 3 | 22 | 2 |
| 87 | 4 | 23 | 2 |
| 88 | 9 | 25 | 3 |
| 89 | 2 | 26 | 2 |
| 90 | 1 | | |
| 91 | 2 | | |
| Average | 3.4 | Average | 2.2 |
| St. dv | 2.2 | St. dv | 1.1 |

The invention claimed is:

1. A vector for plant transformation comprising (i) a T-DNA sequence comprising a sequence located between two direct repeats and (ii) an antisense housekeeping gene, wherein the housekeeping gene is selected from the group consisting of an ATP synthase gene, a cytochrome c gene, a pyruvate kinase gene, an aminoacyl transferase gene, a phosphate translocator gene, a dicarboxylate translocator gene, and a 2-oxo-glutarate translocator gene, wherein said antisense housekeeping gene is not located within said T-DNA sequence.

2. The vector of claim 1, wherein said housekeeping gene is an ATP synthase gene.

3. The vector of claim 1, wherein said housekeeping gene is a cytochrome c gene.

4. The vector of claim 1, wherein said housekeeping gene is a pyruvate kinase gene.

5. The vector of claim 1, wherein said housekeeping gene is an aminoacyl transferase gene.

6. The vector of claim 1, wherein said housekeeping gene is an phosphate translocator gene.

7. The vector of claim 1, wherein said housekeeping gene is a dicarboxylate translocator gene.

8. The vector of claim 1, wherein said housekeeping gene is a 2-oxo-glutarate translocator gene.

* * * * *